Figure 1:
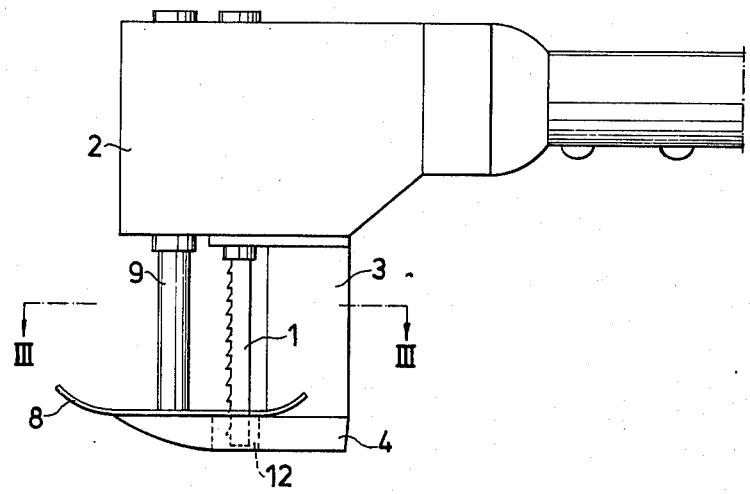

United States Patent

Persson

[11] 3,973,324
[45] Aug. 10, 1976

[54] SAWING APPARATUS

[76] Inventor: Curt Persson, Storegardsvagen 86, S-461 00 Trollhattan, Sweden

[22] Filed: Dec. 3, 1974

[21] Appl. No.: 529,248

[30] Foreign Application Priority Data

Dec. 4, 1973 Sweden............................ 7316346

[52] U.S. Cl.................................. 30/370; 30/275
[51] Int. Cl.² ...................... B23D 49/16; B26B 7/00
[58] Field of Search................. 30/166, 166 A, 392, 30/393, 275, 370

[56] References Cited
UNITED STATES PATENTS

| | | | |
|---|---|---|---|
| 1,951,880 | 3/1934 | Niederhofer.......................... | 30/370 |
| 2,217,923 | 10/1940 | Silverman.......................... | 30/275 X |
| 2,480,278 | 8/1949 | Zawistowski....................... | 30/275 X |
| 2,659,969 | 11/1953 | Merkur............................. | 30/275 X |
| 3,533,161 | 10/1970 | Magnin............................. | 30/166 |

FOREIGN PATENTS OR APPLICATIONS

720,708  12/1954  United Kingdom.................. 30/166

*Primary Examiner*—Al Lawrence Smith
*Assistant Examiner*—J. C. Peters
*Attorney, Agent, or Firm*—Cushman, Darby & Cushman

[57] ABSTRACT

A saw for cutting off plaster casts and the like. A single freely reciprocal sawblade is driven by a motor for providing cutting of a cast of the like. A flat guiding plate is disposed in the same vertical plane as the sawblade, and is spaced from the rear of the blade, a lower anvil is provided for engagement with the bottom surface of a cast being cut and for guiding the reciprocatory motion of the sawblade, and a spring-pressed gliding plate is disposed generally forwardly of the blade and engages the upper surface of a cast being cut. The gliding plate and anvil overlap over a substantial length thereof, and firmly hold the cast in place during cutting.

3 Claims, 3 Drawing Figures

SAWING APPARATUS

The present invention relates to an apparatus for cutting up a plaster cast or object formed in a similar way.

In medical care, the removal of plaster casts of different types and sizes often occurs. The method of approach in cutting up such casts has been united with a number of drawbacks and discomfort. Cutting and pinching injuries can easily occur if the operator is not careful, but even carefulness does not always help, since the apparatuses used for the purpose up to now are primitive or designed so that injuries can easily occur. There are so-called plaster cutters or pincers, but they are clumsy and heavy and are therefore troublesome to cut with, especially if the cast is a heavy one. Such aids easily cause pressure and pinching injuries. There are also special plaster saws. One such, of the circular saw type, has no guard for the underlying portion of the body, and it is therefore risky to use it. Another such saw has a guard, but this is provided with a hinged end piece which is supposed to follow the body portion contour, but probably does not do so. Neither is it made so that it can get through the bandage and wadding which is generally used in connection with a plaster cast. Neither does the device have a stop on the upper side, for which reason manoeuvreability will be poor. Such a stop is also lacking in a saw of the sabre type, where two blades move in an open sleeve. This saw is hardly suitable for cutting in plaster, since the edges of the sleeve will knock against the sides of the cut.

The drawbacks with currently known and used apparatuses for cutting up plaster casts and the like, now set forth, have been completely eliminated by the sawing device according to the invention, which is easy to use and with the help of which a plaster cast can be cut through along its whole length without a break and without risk for injury or discomfort. By making two cuts, a cast can be parted into two portions or halves, which can easily be removed, the portion of the body having been in plaster can be exposed without the need of recoursing to breaking up the cast. The apparatus therefore brings with it great savings in time and work. The distinguishing features of the apparatus are apparent from the following patent claims.

Figure 2:
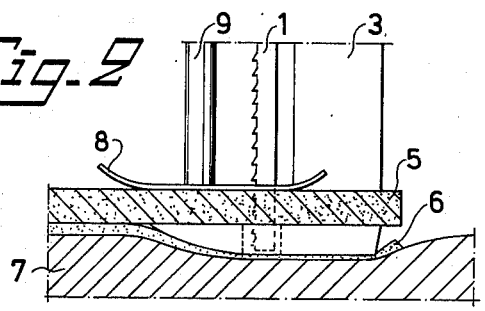

An advantageous embodiment of the apparatus according to the invention will now be more closely described while referring to the accompanying drawing, where FIG. 1 shows the sawing apparatus from one side, when it is not in use, and FIG. 2 shows the lower part of the same apparatus while at work on a plaster cast.

Figure 3:
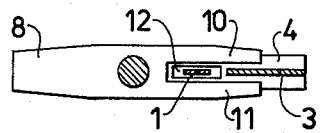

In FIG. 3 is shown a section A—A of FIG. 1, where the gliding plate, foot, saw blade and guiding plate may be seen from above.

The apparatus shown comprises a saw blade 1, which is attached to a sawing head 2. This houses a coupling and reducing device for transmitting a reciprocating motion to the saw blade. Driving is done most simply by an electric motor which can be attached to the sawing head and directly coupled to the coupling and reducing device, or it can drive the device via a flexible shaft. Behind the rear edge of the sawblade and in the same plane as it, a flat guiding plate 3 is attached by one end to the sawing head. At the other end of the plate and at right angles to it, there is attached a rounded foot 4 extending a distance past the sawblade and terminating in a wedge-shaped portion. There is a slot 12 in the foot 4 enabling complete sawing-through of the plaster cast 5, 6 or the material, without damage to the underlying portion 7. The sawblade 1 is fitted to the sawing head 2 so that its stroke is on the return before its free end reaches the lower surface of foot 4.

At the sawing head there is also a spring loaded rod 9 slidably attached at one end, the other end being provided with a gliding plate 8 mounted at right angles to the rod. The ends of the gliding plate are bent in the direction of the sawing head 2, while its end facing the guiding plate is bifurcated into arms 10, 11 with a space between for the sawblade 2 and the guiding plate 3.

When the apparatus is to be used for cutting up a plaster cast 5, 6, the foot 4 is moved with its narrow end in under the cast, and here it can be suitable to search for the place between the plaster shell 5 itself and the layer of wadding 6 possibly lying underneath. A person having a plaster cast which is to be removed in this way hardly feels anything of the procedure.

I claim:

1. Sawing apparatus for cutting a plaster cast or the like having upper and lower surfaces, said apparatus comprising a single freely reciprocating sawblade, having a forward toothed edge and a rear smooth edge, means for operatively coupling said sawblade to a saw head, means in said saw head for driving said sawblade in its reciprocating motion, a flat guiding plate disposed in the same vertical plane as said sawblade and operatively connected to said saw head at one end thereof, and spaced from said sawblade rear end along the entire length thereof, means for guiding reciprocatory motion of said sawblade and for providing a lower anvil in the direction of sawing between said plaster cast or the like and any structure over which the plaster cast or the like is disposed, and engaging the lower surface of said plaster cast or the like, said means being operatively connected to said guiding plate at an end thereof opposite said end connected to said saw head, and extending forwardly from said guiding plate past the forward toothed edge of said sawblade, and a spring-pressed gliding plate disposed generally forwardly of said sawblade for engaging the upper surface of said plaster cast or the like when said means for providing a lower anvil engages the bottom surface of said plaster cast or the like, said gliding plate having a split rear portion thereof straddling said sawblade, a portion thereof being disposed on either side of said sawblade, and wherein said means for providing an anvil and said gliding plate overlap over a substantial portion of the lengths thereof.

2. Apparatus as recited in claim 1 wherein said gliding plate is spring-pressed by a spring loaded rod acting at a point thereof, said spring loaded rod extending downwardly from said sawhead, and the point of action of said spring loaded rod on said gliding plate being disposed over a forward portion of said means for providing an anvil.

3. Apparatus as recited in claim 2 wherein said forward portion of said means for providing an anvil is rounded and has a pointed forward tip, and wherein said gliding plate has upwardly curved forward and rearward portions.

* * * * *